United States Patent
Han et al.

(10) Patent No.: US 12,324,666 B2
(45) Date of Patent: Jun. 10, 2025

(54) FATIGUE MEASUREMENT METHOD, APPARATUS, AND COMPUTER-READABLE MEDIUM

(71) Applicant: Lenovo (Beijing) Limited, Beijing (CN)

(72) Inventors: Xing Han, Beijing (CN); Wenrui Liu, Beijing (CN)

(73) Assignee: LENOVO (BEIJING) LIMITED, Beijing (CN)

( * ) Notice: Subject to any disclaimer, the term of this patent is extended or adjusted under 35 U.S.C. 154(b) by 496 days.

(21) Appl. No.: 17/678,951

(22) Filed: Feb. 23, 2022

(65) Prior Publication Data
US 2022/0386918 A1 Dec. 8, 2022

(30) Foreign Application Priority Data
Jun. 2, 2021 (CN) .......................... 202110613718.8

(51) Int. Cl.
*A61B 5/00* (2006.01)
*A61B 5/22* (2006.01)
*G06F 18/25* (2023.01)

(52) U.S. Cl.
CPC ............ *A61B 5/222* (2013.01); *A61B 5/7203* (2013.01); *G06F 18/253* (2023.01)

(58) Field of Classification Search
CPC ..... A61B 5/222; A61B 5/7203; G06F 18/253; G06F 382/128
See application file for complete search history.

(56) References Cited

U.S. PATENT DOCUMENTS

| 11,730,381 B1* | 8/2023 | Owsley ................ A61B 5/7257 600/528 |
| 2016/0090097 A1* | 3/2016 | Grube ................... B60W 40/08 340/576 |
| 2022/0338757 A1* | 10/2022 | Kim ........................ G16H 50/30 |

FOREIGN PATENT DOCUMENTS

| CA | 3181091 A1 * | 12/2021 | ............. A61B 5/021 |
| CN | 112819790 B * | 9/2022 | ............. A61B 5/024 |
| KR | 20200061016 A * | 6/2020 | |
| WO | WO-2004089212 A1 * | 10/2004 | ............. A61B 5/087 |
| WO | WO-2018179150 A1 * | 10/2018 | ............... A61B 5/02 |

* cited by examiner

*Primary Examiner* — Khai M Nguyen
(74) *Attorney, Agent, or Firm* — ANOVA LAW GROUP, PLLC

(57) ABSTRACT

A fatigue measurement method includes obtaining a face video of a target object, processing the facial video to obtain a plurality of quasi-heart rates and a plurality of quasi-vibration frequencies, selecting a target heart rate from the plurality of quasi-heart rates and a target vibration frequency from the plurality of quasi-vibration frequencies, detecting the target heart rate and the target vibration frequency, and determining, according to the detection result, that the target object is in a fatigue state. The quasi-heart is obtained through one or more of a region of interest (ROI) between eyebrows and an ROI of chin, and the quasi-vibration frequency obtained through one or more of an ROI of eyes and an ROI of mouth.

17 Claims, 4 Drawing Sheets

FATIGUE MEASUREMENT METHOD, APPARATUS, AND COMPUTER-READABLE MEDIUM

CROSS-REFERENCE TO RELATED DISCLOSURE

The present disclosure claims the priority to Chinese Patent Disclosure No. 202110613718.8, entitled "Fatigue Measurement Method, Apparatus, and Computer-Readable Medium", filed on Jun. 2, 2021, the entire content of which is incorporated herein by reference.

TECHNICAL FIELD

The present disclosure relates to the technical field of artificial intelligence, and in particular, to a fatigue measurement method, a apparatus and a computer-readable medium.

BACKGROUND

At present, during the pandemic prevention period of the new coronavirus, both work and study are affected by the epidemic. For this reason, everyone has started various cloud office, cloud class and cloud play. Cloud class has become the main form of class for students during the pandemic. Cloud classes are realized through online classes, and online classes are usually recorded and broadcast. For this reason, students and teachers cannot establish face-to-face interactions. For elementary and middle school students with weak self-control, they often experience fatigue in class during the day due to playing mobile phones or games all night, resulting in inability to concentrate, which in turn affects their learning. Therefore, there is an urgent need to provide a fatigue detection method, which can detect the degree of fatigue of students during online classes to closely monitor the physical and physical states of students, to help strengthen autonomous learning of students and help students develop good study habits.

At present, fatigue monitoring technology is mainly used in drone driving. It mainly detects the fatigue characteristics of eyes, mouth and head, and then judges the degree of fatigue through complex logical analysis. However, this serial logic analysis may not only be low robust but also be cumbersome and may neglect the relationship between the eyes and the mouth, and hence it cannot accurately detect the fatigue state.

SUMMARY

According to one aspect of the present disclosure, a fatigue measurement method is provided. The fatigue measurement method includes obtaining a face video of a target object, processing the facial video to obtain a plurality of quasi-heart rates and a plurality of quasi-vibration frequencies, selecting a target heart rate from the plurality of quasi-heart rates and a target vibration frequency from the plurality of quasi-vibration frequencies, detecting the target heart rate and the target vibration frequency, and determining, according to the detection result, that the target object is in a fatigue state. The quasi-heart is obtained through one or more of a region of interest (ROI) between eyebrows and an ROI of chin, and the quasi-vibration frequency obtained through one or more of an ROI of eyes and an ROI of mouth.

According to another aspect of the present disclosure, a fatigue measurement apparatus is provided. The fatigue measurement apparatus includes an acquisition module configured to obtain a face video of a target object, a processing module configured to process the face video to obtain a plurality of quasi-heart rates and a plurality of quasi-vibration frequencies, a selection module configured to select a target heart rate from the plurality of quasi-heart rates and a target vibration frequency from the plurality of quasi-vibration frequencies, and a detection module configured to detect the target heart rate and the target vibration frequency, and determine that the target object is in a fatigue state according to the detection result. The quasi-heart rate obtained through one or more of a region of interest (ROI) between the eyebrows and an ROI of the chin, wherein the quasi-vibration frequencies is obtained through one or more of an ROI of eyes and an ROI of mouth.

According to further aspect of the present disclosure, a non-transitory computer-readable medium is provided. The medium stores a computer program, when executed by a processor, causing the processor to obtain a face video of a target object, process the facial video to obtain a plurality of quasi-heart rates and a plurality of quasi-vibration frequencies, select a target heart rate from the plurality of quasi-heart rates and a target vibration frequency from the plurality of quasi-vibration frequencies, detect the target heart rate and the target vibration frequency, and determine, according to the detection result, that the target object is in a fatigue state. The quasi-heart is obtained through one or more of a region of interest (ROI) between eyebrows and an ROI of chin, and the quasi-vibration frequency obtained through one or more of an ROI of eyes and an ROI of mouth.

BRIEF DESCRIPTION OF THE DRAWINGS

The accompanying drawings are used for better understanding of the present disclosure, and do not constitute an improper limitation of the present disclosure. In the drawings, the same or corresponding reference numerals denote the same or corresponding parts.

DETAILED DESCRIPTION OF THE EMBODIMENTS

Exemplary embodiments of the present disclosure are described below with reference to the accompanying drawings, which include various details of the embodiments of the present disclosure for facilitating understanding and should be considered as exemplary only. Accordingly, those of ordinary skill in the art will recognize that various changes and modifications of the embodiments described herein can be made without departing from the scope and spirit of the disclosure. Also, descriptions of well-known functions and constructions may be omitted from the following description for clarity and conciseness.

Figure 1:
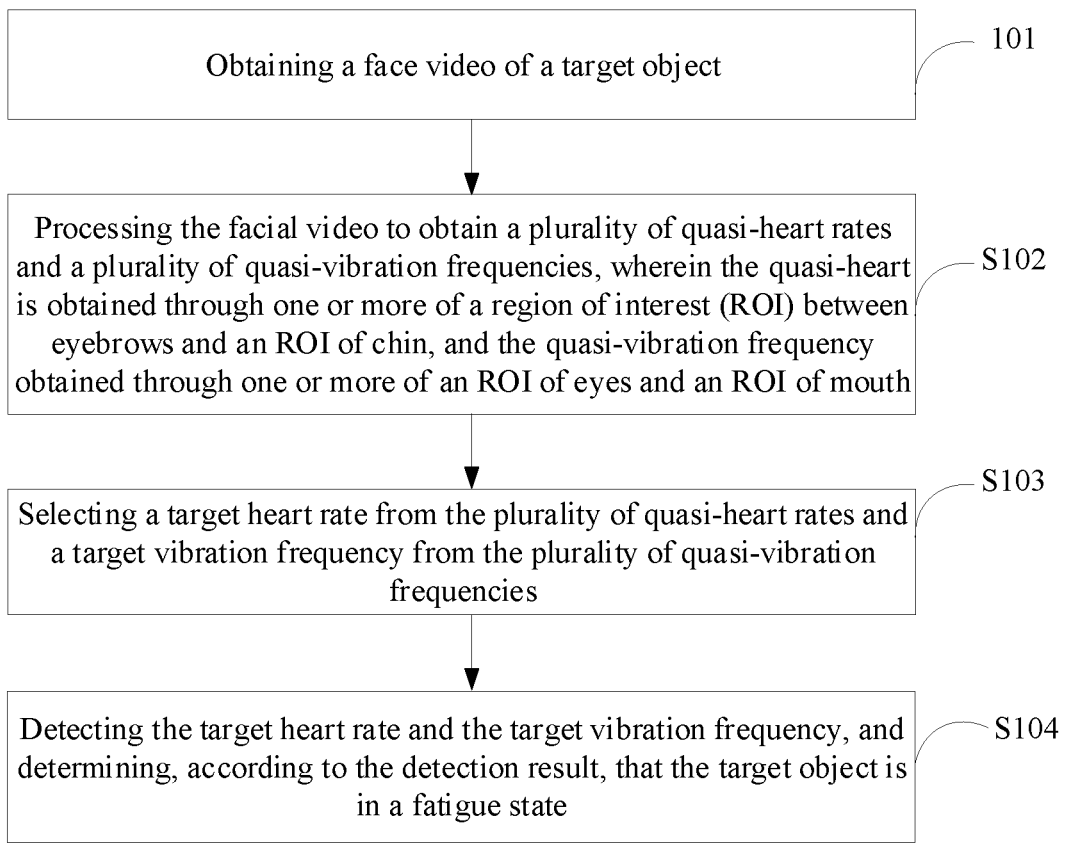
FIG. 1 is a schematic flowchart of a fatigue measurement method according to an embodiment of the present disclosure.

As shown in FIG. 1, a schematic flowchart of a fatigue measurement method according to an embodiment of the present disclosure is shown. A method for measuring fatigue, including the following operation procedures: S101, obtaining a face video of a target object; S102, processing the face video to obtain a plurality of quasi-heart rates and a plurality of quasi-vibration frequencies, where the quasi-heart rate is obtained through using a region of interest (ROI) between eyebrows and/or an ROI of chin, and the quasi-vibration frequency is obtained through using an ROI of eyes and/or an ROI of mouth; S103, selecting a target heart rate from the plurality of quasi-heart rates, and selecting a target vibration frequency from the plurality of quasi-vibration frequencies; S104, detecting the target heart rate and the target vibration frequency, and determining that the target object is in a fatigue state according to the detection result.

In S101, the face video is configured to indicate the face video within a certain period of time.

In S102, there can be various implementation manners for obtaining the plurality of quasi-heart rates and the plurality of quasi-vibration frequencies through the face video, which are not limited here.

For example, the face video may be divided into a plurality of window videos according to a time window of a specific step size. For any window video, the window video may be extracted and processed to obtain an eye feature signal, a mouth feature signal, an eyebrow feature signal, and a chin feature signal. The quasi-heart rate can be obtained after extracting and processing the eyebrow feature signal, or after processing the chin feature signal, or after extracting and processing the eyebrow feature signal and the chin feature signal. The quasi-vibration frequency may be obtained after extracting and processing the eye feature signal, or after extracting and processing the mouth feature signal, or after extracting and processing the eye feature signal and the mouth feature signal. Since each window video corresponds to a quasi-heart rate and a quasi-vibration frequency, a plurality of window videos correspond to the plurality of quasi-heart rates and the plurality of quasi-vibration frequencies. Therefore, the quasi-heart rate and quasi-vibration frequency of the face video can be counted by means of a sliding window, which can not only detect the fatigue state in real-time, but can also obtain a more robust fatigue measurement result.

It should be noted that, since the face video is a temporal sequence formed by multiple frames of face images arranged in time sequence, and the window video is obtained through dividing the face video according to the time window of the specific step size, the plurality of quasi-heart rates and the plurality of quasi-vibration frequencies corresponding to the face video are all temporal sequences.

In S103, denoising may be performed on several quasi-heart rates and several quasi-vibration frequencies, respectively, to obtain a target heart rate and a target vibration frequency. There can be various ways of denoising, which are not limited here, as long as discrete values in the plurality of quasi-heart rates and discrete values in the plurality of quasi-vibration frequencies can be removed.

There can be several target heart rates obtained after removing discrete values, several target vibration frequencies obtained after removing discrete values, and several target heart rates and several target vibration frequencies can also be temporal sequences.

In S104, the target heart rate and the target vibration frequency may be respectively detected, and if the detection result indicates that the target heart rate meets a first preset heat rate threshold and the target vibration frequency meets a first preset vibration frequency threshold, it can determined that the target object is in a fatigue state. Classification of fatigue state levels may be determined according to the actual measurement requirements.

For example, the fatigue state can be divided into a mild fatigue state and a micro-sleep state. A normal heart rate and a normal vibration frequency of the target object may be obtained when the target object is in a non-fatigue state. A difference between the normal heart rate and the target heart rate and a difference between the normal vibration frequency and the target vibration frequency may be determined respectively. In some embodiments, if within preset measurement times, the difference corresponding to the target heart rate measured each time is greater than a second preset heart rate threshold and the difference corresponding to the target vibration frequency measured each time within preset measurement times is greater than a second preset vibration threshold, it can be determined that the target object is in a mild fatigue state. For example, in three consecutive window videos, the difference corresponding to the target heart rate measured in each window video is greater than the second preset heart rate threshold, and the difference corresponding to the target vibration frequency measured in each window video is greater than the second preset vibration threshold, it can be determined that the target object is in the mild fatigue state. In some other embodiments, if within the preset measurement times, the difference corresponding to the target heart rate measured each time is greater than a third preset heart rate threshold and the difference corresponding to each measured target vibration frequency is greater than a third preset vibration threshold, it can be determined that the target object is in a micro-sleep state.

It should be noted that one window video corresponds to one target heart rate and one vibration frequency, and the plurality of window videos correspond to the plurality of target heart rates and the plurality of vibration frequencies.

According to some embodiments of the present disclosure, a plurality of quasi-heart rates and a plurality of quasi-vibration frequencies can be obtained through processing the facial video, and a target heart rate and a target vibration frequency may be selected from the plurality of quasi-heart rates and the plurality of quasi-vibration frequencies respectively. The target heart rate and the target vibration frequency may be detected, and it can be determined that the target object is in a fatigue state according to the detection result. Accordingly, the heart rate and the vibration frequency of the eyes and mouth can be combined for the detection of the fatigue state of the target object, thereby improving the accuracy and robustness of the fatigue measurement results, which solves the problems in the existing technologies that the amount of calculation may be increased due to complex logic analysis and the robustness of the fatigue measurement results may be low.

Figure 2:
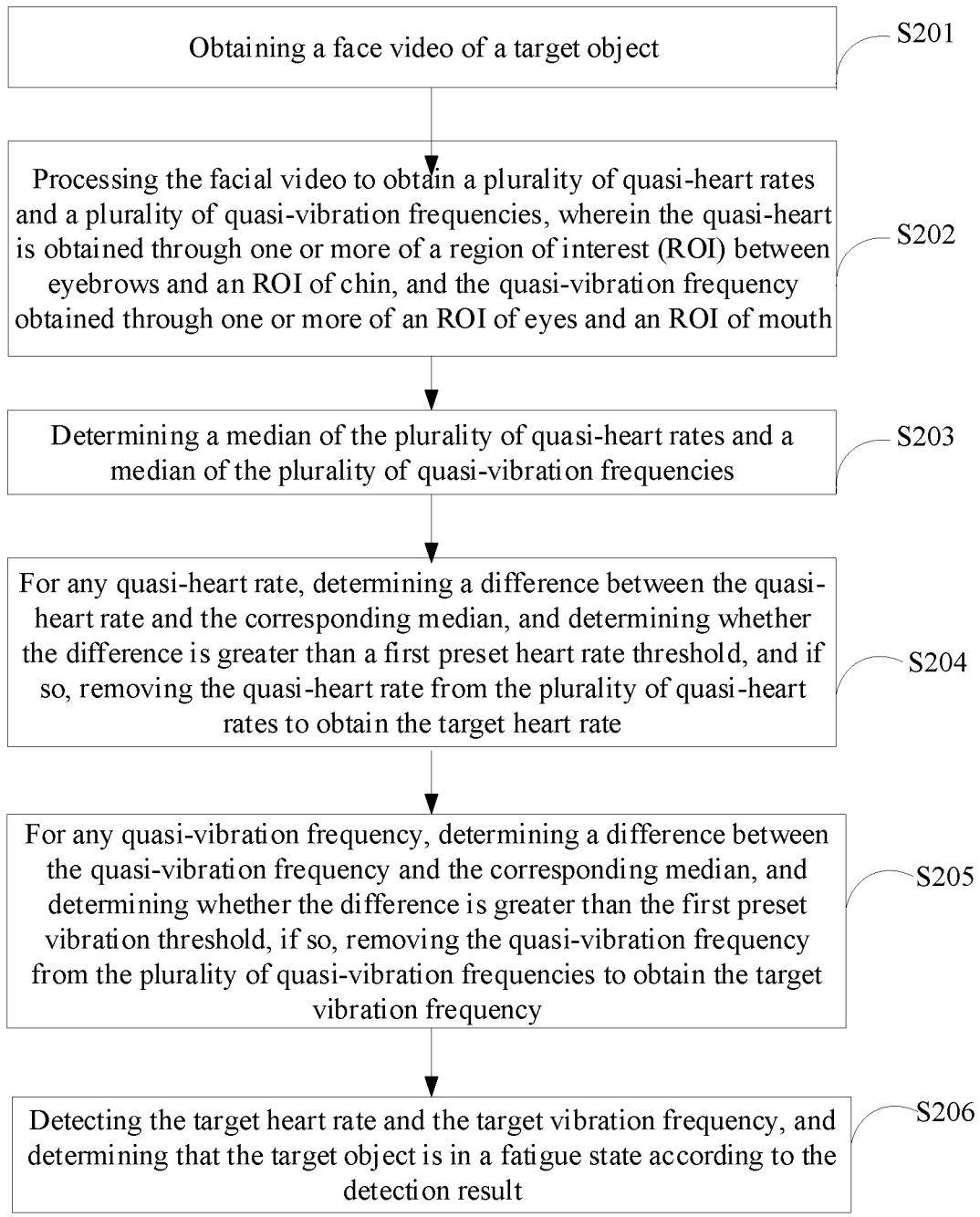
FIG. 2 is a schematic flowchart of the fatigue measurement method according to another embodiment of the present disclosure.

FIG. 2 illustrates a schematic flowchart of the fatigue measurement method according to some embodiments of the present disclosure. Such embodiments may be further optimized based on the foregoing embodiments. As shown in FIG. 2, a fatigue measurement method may include at least the following operation flow: S201, obtaining a face video of a target object; S202, processing the face video to obtain a plurality of quasi-heart rates and a plurality of quasi-vibration frequencies, where the quasi-heart rate is obtained through the ROI between eyebrows and the ROI of chin, and the quasi-vibration frequency is obtained through the ROI of eyes and/or the ROI of mouth; S203, determining a median of the plurality of quasi-heart rates and a median of the plurality of quasi-vibration frequencies; S204, for any quasi-heart rate, determining a difference between the quasi-heart rate and the corresponding median, and determining whether the difference is greater than a first preset heart rate threshold, and if so, removing the quasi-heart rate from the plurality of quasi-heart rates to obtain the target heart rate; S205, for any quasi-vibration frequency, determining a difference between the quasi-vibration frequency and the corresponding median, and determining whether the difference is greater than the first preset vibration threshold, if so, removing the quasi-vibration frequency from the plurality of quasi-vibration frequencies to obtain the target vibration frequency; S206, detecting the target heart rate and the target vibration frequency, and determining that the target object is in a fatigue state according to the detection result.

The specific implementation process of S201 to S202 is similar to the specific implementation process of S101 and S102 according to the embodiments as shown in FIG. 1, and details will not be described here.

In S203 to S205, effective denoising may be performed on the plurality of quasi-heart rates or the plurality of quasi-vibration frequencies, so that the target heart rate or the target vibration frequency can be accurately obtained.

In S206, a normal heart rate and a normal vibration frequency of the target object may be obtained when the target object is in a non-fatigue state. A difference between the normal heart rate and the target heart rate and a difference between the normal vibration frequency and the target vibration frequency may be determined respectively. The difference corresponding to the target heart rate and the difference corresponding to the target vibration frequency can be detected. If the detection result indicates that within preset measurement times, the difference corresponding to the target heart rate measured each time is greater than a second preset heart rate threshold and the difference corresponding to the target vibration frequency measured each time is greater than a second preset vibration threshold, it can be determined that the target object is in a state of mild fatigue. If within the preset measurement times, the difference corresponding to the target heart rate measured each time is greater than a third preset heart rate threshold and the difference corresponding to the measured target vibration frequency is greater than a third preset vibration threshold, it can be determined that the target object is in a micro-sleep state. The third preset heart rate threshold is greater than the second preset heart rate threshold, and the third preset vibration threshold is greater than the second preset vibration frequency threshold.

It should be noted that, when the difference corresponding to the target vibration frequency measured each time is greater than the second preset vibration threshold, the target vibration frequency at this time has dropped to a single digit. When the value is greater than the third preset vibration threshold, the target vibration frequency at this time has dropped to 0.

In the above embodiments, the difference corresponding to the target heart rate and the difference corresponding to the target vibration frequency can be measured, and the two differences can be detected, and then the fatigue state level of the target object can be determined based on the detection result and different preset thresholds. Accordingly, the level of the fatigue state of the target object can be determined based on different preset thresholds, so that the fatigue state of the target object can be accurately detected, and the accuracy of the fatigue detection of the target object can be improved.

Figure 3:
FIG. 3 is a schematic flowchart of determining a quasi-heart rate and a quasi-vibration frequency according to an embodiment of the present disclosure.

FIG. 3 illustrates a schematic flowchart of determining a quasi-heart rate and a quasi-vibration frequency according to some embodiments of the present disclosure. Such embodiments may be further optimized based on the foregoing embodiments. Determining the quasi-heart rate and the quasi-vibration frequency may include at least the following operation process: S301, using the model to predict the window video, and generating face key points, the face key points including contour key points and specific part key points; S302, extracting eye key points, mouth key points, the ROI between eyebrows, and the ROI of chin respectively from the face key points; S303, performing dimension reduction processing on the eye key points and the mouth key points respectively to obtain an eye feature signal and a mouth feature signal; S304, performing feature extraction processing on the ROI of eyebrows and the ROI of chin, respectively to obtain an eyebrow color signal and a chin color signal; S305, performing noise reduction processing on the eyebrow color signal and the chin color signal respectively to obtain an eyebrow feature signal and a chin feature signal; S306, performing fusion processing on the eye feature signal, the mouth feature signal, the eyebrow feature signal, and the chin feature signal to obtain a fused feature signal; S307, performing noise reduction processing on the fused feature signal to obtain a smooth feature signal; S308, performing blind source separation on the smooth feature signal, and converting signal components after blind source separation into frequencies to obtain a plurality of frequencies; S309, selecting a pre-heart rate from a plurality of frequencies based on a body heart rate range, and averaging the selected pre-heart rate to obtain a quasi-heart rate, and selecting a pre-vibration frequency from a plurality of frequencies based on a range of the eye vibration frequency and a range of the mouth vibration frequency, and averaging the pre-vibration to obtain a quasi-vibration frequency.

In S301, the training process of the multi-task network model may be as follows: obtaining a first face image marked with key points of facial contours, and using the first face image as a first training sample; obtaining a second face image marked with key points of specific parts, and using the second face image as a second training sample; inputting the first training sample and the second training sample simultaneously into the multi-task network for model training to obtain the multi-task network model. Therefore, sharing the model through multiple tasks can enable information sharing and information supplementation between the first training sample and the second training sample, so that pixels of the key points of the face can be stabilized, and offset of the key points of the face during the training process can be slowed down. The calculation amount of the multi-task network can be further reduced, and the logical reasoning speed of the multi-task network can be increased, which improves the accuracy of model training.

Face images may be extracted from the window video and a plurality of frames of face images may be obtained. Each frame of face images may be normalized, and the normalized face images may be input into the trained multi-task network model for prediction. Key points of the face can be generated, which include contour key points and specific part key points. Therefore, by dividing the face video into a plurality of window videos for processing according to the time window of a specific step size, the processing speed of the multi-task network model can be improved, which is favorable to realizing real-time measurement. Then the window video can be normalized, thereby reducing dimensions of all face image pixels in the window video, thereby reducing the difference between multiple face images in the input multi-task network model and improving the prediction accuracy of the multi-task network model.

To more effectively detect the fatigue state of the target object in real-time, the resolution of the normalized face image can also be adjusted, for example, the resolution of the normalized face image may be adjusted to 320×240. Accordingly, under the condition of ensuring the pixel accuracy of the face image, the logical reasoning time of the multi-task network model can be reduced, and the fatigue state can be detected in real-time based on the face video.

In S302, left eye key points, right eye key points, and mouth key points may be selected from the specific part key points based on a key point index, and the left eye key points and the right eye key points can be determined as the eye key points. For example, there can be 98 face key points generated by model prediction. According to the key point index, 9 key points are selected from the 98 key points to form the left eye area, 9 key points to form the right eye area, and 20 key points to form the mouth area. Based on the contour key points, and left eyebrow key points and right eyebrow key points of the specific part key points, the ROI between the eyebrows and below the forehead can be determined, and the ROI of the chin can be determined based on the contour key points and the mouth key points. Accordingly, the eye key points, the mouth key points, the ROI between the eyebrows, and the ROI of the chin can be accurately obtained through means of index query.

Both the eye key points and the mouth key points can be represented by point coordinates. Both the ROI of the eyebrows and the ROI of the chin may be based on multiple point coordinates to form the regions.

In S303, the eye key points may include semantic information of an aspect ratio of the eyes, and the mouth key points may include semantic information of an aspect ratio of the mouth. Since one key point corresponds to one feature signal, 18 eye key points correspond to 18 eye feature signals, and 20 mouth key points correspond to 20 mouth feature signals.

The eye key points and mouth key points can be converted from two-dimensional vectors to one-dimensional vectors through dimension reduction processing, which is favorable to the fusion of the eye feature signal, the mouth feature signal, the eyebrow feature signal and the chin feature signal in the later stage.

In S304, the ROI between eyebrows and the ROI of chin may be respectively converted into hue, saturation, value (HSV) format. The pixel values of the three channels (for example, the hue channel, the saturation channel and the value channel) of the ROI between the eyebrows in the HSV format may be averaged respectively to obtain a first hue signal, a first saturation signal, and a first value signal, and the first hue signal, the first saturation signal and the first value signal may be determined as the eyebrow color signal. The three channels of the ROI of chin with HSV format can be averaged respectively to obtain a second hue signal, a second saturation signal, and a second value signal, and the second hue signal, the second saturation signal, and the second value signal may be determined as the chin color signal. Since one ROI corresponds to three feature signals, two ROIs correspond to six feature signals.

Since brightness and saturation are highly sensitive to dynamically blurred images, by converting the two ROIs into HSV format, the face images with blurred ROIs in the window video can be effectively removed, to solve the problem of displaying motion blurred face images in the window video that leads to inaccurate heart rate calculations.

In S305, there can be many ways to implement noise reduction. Noise reduction can be performed by variance selection, or noise reduction can be performed by decentralization, or noise reduction can be performed by variance selection and decentralization in combination.

Since both the eyebrow color signal and the chin color signal correspond to the window video, and the window video is temporal, the eyebrow color signal and the chin color signal are also temporal. The eyebrow color signal is segmented according to a time window of a specific step size to obtain a plurality of eyebrow sub-color signals. For any eyebrow sub-color signal, a variance between the saturation signal and the brightness signal corresponding to the eyebrow sub-color signal may be calculated. If the variance is greater than a preset threshold, a corresponding segment of the eyebrow sub-color signal may be removed from the eyebrow color signal. The remaining eyebrow sub-color signals may be spliced to obtain the eyebrow signal. The chin color signal may be segmented according to a window time of a specific step size, and a plurality of chin color signals may be obtained. For any chin sub-color signal, the variance between the saturation signal and the brightness signal corresponding to the chin sub-color signal may be calculated. If the variance is greater than a predetermined threshold, a corresponding segment of the chin sub-color signal may be removed from the chin color signal. The remaining chin sub-color signals may be spliced to obtain the chin signal. Accordingly, by means of variance selection, abnormal values caused by motion blur in the window video can be effectively removed, and the accuracy of heart rate calculation can be improved.

The eyebrow signal can be segmented according to a time window of a specific step size, and a plurality of eyebrow sub-signals may be obtained. For any eyebrow sub-signal, an HSV mean value of the eyebrow sub-signal may be calculated, and obtain a difference between the HSV corresponding to each position in the eyebrow sub-signal and the HSV mean value, to obtain a decentralized eyebrow sub-signal. A plurality of decentralized eyebrow sub-signals may be spliced to obtain an eyebrow feature signal. The chin signal may be segmented according to a time window of a specific step size, and a plurality of chin sub-signals may be obtained. For any chin sub-signal, an HSV mean value of the chin sub-signal may be calculated, and obtain a difference between the HSV corresponding to each position of the chin sub-signal and the HSV mean value to obtain decentralized chin sub-signal A plurality of decentralized chin sub-signals may be spliced to obtain a chin feature signal. Therefore, through decentralization processing, abnormal values caused by motion blur in the window video can be effectively removed, so that the chin feature and the eyebrow feature in the window video can be more apparent.

In S306, the fusion processing here refers to performing splicing processing on the eye feature signal, the mouth feature signal, the eyebrow feature signal, and the chin feature signal to form a fused feature signal. For example, 18 eye feature signals, 20 mouth feature signals, and 6 feature signals corresponding to two ROIs may be added to obtain a 44-dimensional fusion feature signal.

In S307, each dimensional fusion feature signal in the fused feature signal may be fitted with an axis spline curve to obtain a nonlinear trend signal. The difference between the fused feature signal and the nonlinear trend signal may be used to obtain a nonlinear trend-removed signal. Least squares method may be used to fit the nonlinear trend removed signal to obtain a linear trend signal. A difference between the nonlinear trend-removed signal and the linear trend signal may be used to obtain a linear trend-removed signal. Accordingly, the nonlinear trend in the fused feature signal can be removed by fitting the axis spline curve, which can ensure the linearity of the fused feature signal, then the linear trend in the feature signal may be removed by the least squares method, so that a smooth feature signal similar to a straight line can be obtained, which improves the stability of the signal and avoids the fluctuation of the signal.

After the smooth feature signal is obtained, the smooth feature signal can also be filtered by a filter to filter out ultra-low frequencies and high frequencies in the signal, thereby reducing the influence of the noise signal on the blind source separation.

In S308, independent component analysis (ICA) may be used to perform blind source separation on the smooth feature signal to obtain a plurality of mutually independent signal components. Fourier transform may be performed on each signal component to obtain a frequency corresponding to the signal component. Each signal component corresponds to a frequency, and the plurality of signal components correspond to a plurality of frequencies. The plurality of frequencies include the heart rate, the eye vibration frequency, and the mouth vibration frequency.

In S309, for example, the human heart rate range is 0.75 Hz-2.5 Hz. After analyzing each signal, the signal containing the heart rate may have an obvious peak in the area within the frequency range, while peaks of other signals may be much lower than the mentioned peak. Accordingly, pre-heart rates may be selected from the plurality of frequencies, and the mean value of the selected pre-heart rates may be used to obtain a quasi-heart rate. The vibration frequency range of human eyes and mouth is 0.25 Hz-0.5 Hz, and the vibration frequencies of eyes and mouth are similar, so each signal can be analyzed, and the signal containing the eye vibration frequency and the mouth vibration frequency may have an obvious peak in the vibration frequency range. The peak value may be analyzed to obtain the eye vibration frequency and the mouth vibration frequency. Accordingly, the pre-vibration frequency may be selected from a plurality of frequencies, and the mean value of the selected plurality of pre-vibration frequencies may be used to obtain the quasi-vibration frequency.

In some embodiments, the integrated model of multi-task joint training can be used to predict the key points of the face, which improves the robustness of the measurement results of the key points. The variance selection and decentralization processing of the HSV channel signal of the ROI may also be combined, to effectively remove abnormal values caused by motion blur in the window video, such that the accuracy of heart rate calculation can be improved. Then the fusion feature signal may be processed by the axis spline curve fitting and the least squares method, to remove the nonlinear trend and the linear trend from the fusion feature signal, which ensures the smoothness of the fusion feature signal. Finally, the quasi-heart rate and the quasi-vibration frequency can be obtained through means of blind source separation and denoising, which improves the accuracy of the calculation of quasi-heart rate and quasi-vibration frequency, and in turn improves the accuracy and robustness of the fatigue measurement results.

It should be understood that, in the embodiments of the present disclosure, the size of the sequence numbers of the above-mentioned processes do not imply the execution sequence, and the execution sequence of each process should be determined by its functions and inherent logic, and should not impose any limitation to the embodiments of the present disclosure.

Figure 4:
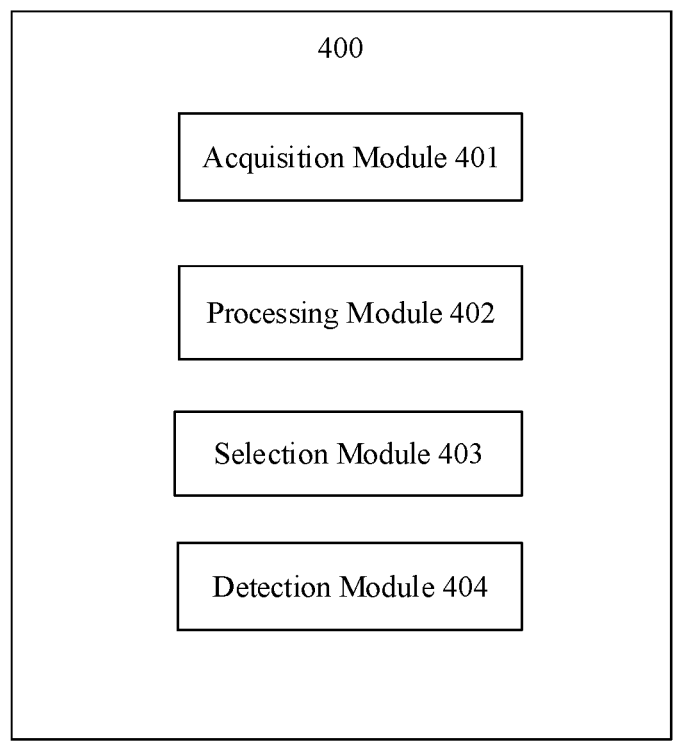
FIG. 4 is a schematic block diagram of a fatigue measurement apparatus according to an embodiment of the present disclosure.

FIG. 4 illustrates a schematic block diagram of a fatigue measurement apparatus according to some embodiments of the present disclosure. A fatigue measurement apparatus 400 may include: an acquisition module 401 configured to acquire a facial video of a target object; a processing module 402 configured to process the facial video to obtain a plurality of quasi-heart rates and a plurality of quasi-vibration frequencies, where the heart rate being is through an eyebrow ROI and/or a chin ROI, and the quasi-vibration frequency is obtained through an eye ROI and/or a mouth ROI; a selection module 403 configured to select a target heart rate from a plurality of quasi-heart rates and select a target vibration frequency from a plurality of quasi-vibration frequencies; and a detection module 404 configured to detect the target heart rate and the target vibration frequency, and determine that the target object is in a fatigue state according to the detection result.

In some embodiments, the processing module 402 may include: a division unit configured to divide the face video into a plurality of window videos according to a time window of a specific step size; a processing unit configured to perform extraction processing on any window video to obtain an eye feature signal, a mouth feature signal, an eyebrow feature signal, and a chin feature signal, and perform fusion processing on the eye feature signal, the mouth feature signal, the eyebrow feature signal, and the chin feature signal to obtain a fusion feature signal, and perform conversion processing on the fusion feature signal to obtain a quasi-heart rate and a quasi-vibration frequency.

In some embodiments, the processing unit may include: a prediction subunit configured to use the model to predict the window video, and generate face key points, where the face key points include contour key points and specific part key points; a first extraction unit configured to extract eye key points, mouth key points, an ROI between the eyebrows, and an ROI of the chin from the face key points respectively; a dimension reduction subunit configured to perform dimension reduction processing on the eye key points and the mouth key points respectively to obtain an eye feature signal and a mouth feature signal; a second extraction subunit configured to perform feature extraction processing on the ROI between the eyebrows and the ROI of the chin, respectively, to obtain an eyebrow color signal and a chin color signal; a third noise reduction sub-unit configured to perform noise reduction processing on the eyebrow color signal and the chin color signal respectively, to obtain the eyebrow feature signal and the chin feature signal.

In some embodiments, the processing unit may further include: a second noise reduction subunit configured to perform noise reduction processing on the fused feature signal to obtain a smooth feature signal; a blind source separation subunit configured to blindly perform noise reduction on the smooth feature signal source separation, and convert signal components after blind source separation into frequencies to obtain a plurality of frequencies; a selection subunit configured to select a pre-heart rate from the plurality of frequencies based on the body's heart rate range, and average the selected pre-heart rate to obtain a quasi-heart rate, select pre-vibration frequencies from the plurality of frequencies based on an eye vibration frequency range and a mouth vibration frequency range, and average the selected pre-vibration frequencies to obtain a quasi-vibration frequency.

In some embodiments, the selection module 403 may include: a determination unit configured to determine a median of the plurality of quasi-heart rates and a median of the plurality of quasi-vibration frequencies; a first selection subunit configured to, for any quasi-heart rate, determine a difference between the quasi-heart rate and the corresponding median, and determine whether the difference is greater than a first preset heart rate threshold, if so, remove the quasi-heart rate from the plurality of quasi-heart rates to obtain a target heart rate; a second selection subunit configured to, for any quasi-vibration frequency, determine a difference between the quasi-vibration frequency and the corresponding median, and determine whether the difference is greater than a first preset vibration threshold, and if so, remove the quasi-vibration frequency from the plurality of quasi-vibration frequencies to obtain a target vibration frequency.

In some embodiments, the detection module 404 may include: an acquisition unit configured to acquire a normal heart rate and a normal vibration frequency of the target object when the target object is in a non-fatigue state; a difference unit configured to determine a difference between the normal heart rate and the target heart rate and a difference between the normal vibration frequency and the target vibration frequency, respectively; a determining unit configured to determine that the target object is in a state of mild fatigue, if within preset measurement times, the difference corresponding to the target heart rate measured each time is greater than a second preset heart rate threshold and the difference corresponding to the target vibration frequency measured each time is greater than a second preset vibration threshold.

The above-mentioned apparatus can execute the fatigue measurement method provided by the embodiments of the present disclosure, and can have corresponding functional modules and beneficial effects for executing the fatigue measurement method. For technical details not described in detail in the present disclosure, reference may be made to the fatigue measurement method provided by the embodiments of the present disclosure.

According to another aspect of the embodiments of the present disclosure, a non-transitory computer-readable storage medium may be provided, a computer program may be stored on the storage medium. When the program is executed by a processor, the processor causes the processor to perform at least the following operation steps: S101, obtaining a target face video of the subject; S102, processing the face video to obtain a plurality of quasi-heart rates and a plurality of quasi-vibration frequencies, where the quasi-heart rate is obtained through an ROI between eyebrows and/or the ROI of chin, and the quasi-vibration frequency is obtained through an ROI of eyes and/or an ROI of mouth; S103, selecting a target heart rate from a plurality of quasi-heart rates, and selecting a target vibration frequency from a plurality of quasi-vibration frequencies; S104, detecting the target heart rate and the target vibration frequency, and determining that the target object is in a fatigue state according to the detection result.

In the description of this specification, description with reference to the terms "one embodiment," "some embodiments," "example," "specific example," or "some examples," etc., mean that specific features described in connection with the embodiments or examples, structures, materials, or features are included in at least one embodiment or one example of the present disclosure. Furthermore, the particular features, structures, materials or characteristics described may be combined in any suitable manner in any one or more embodiments or examples. Furthermore, those skilled in the art may combine different embodiments or examples described in this specification, as well as the features of different embodiments or examples, without conflicting each other.

In addition, the terms "first" and "second" are only used for descriptive purposes, and should not be construed as indicating or implying relative importance or implying the plurality of indicated technical features. Thus, a feature modified with "first", "second" may expressly or implicitly include at least one such feature. In the description of the present disclosure, "plurality" means two or more, unless otherwise expressly and specifically defined.

The above are only specific embodiments of the present disclosure, but the protection scope of the disclosure is not limited by the disclosure. Any changes or replacements a person skilled in the art can make effortlessly within the technical scope of the disclosure should be covered by the protection scope of the disclosure. Therefore, the protection scope of the disclosure should be subject to the protection scope of the accompanying claims.

What is claimed is:

1. A fatigue measurement method, comprising:
    obtaining a face video of a target object;
    processing the facial video to obtain a plurality of quasi-heart rates and a plurality of quasi-vibration frequencies, wherein the quasi-heart is obtained through one or more of a region of interest (ROI) between eyebrows and an ROI of chin, and the quasi-vibration frequency is obtained through one or more of an ROI of eyes and an ROI of mouth;
    selecting a target heart rate from the plurality of quasi-heart rates and a target vibration frequency from the plurality of quasi-vibration frequencies; and
    detecting the target heart rate and the target vibration frequency, and determining, according to the detection result, that the target object is in a fatigue state,
    wherein processing the face video to obtain the plurality of quasi-heart rates and the plurality of quasi-vibration frequencies, comprising:
        dividing the face video into a plurality of window videos according to a time window of a specific step size; and
        performing, for each window video of the plurality of window videos, extraction processing on the each window video to obtain an eye feature signal, a mouth feature signal, an eyebrow feature signal, and a chin feature signal, fusing the eye feature signal, the mouth feature signal, the eyebrow feature signal, and the chin feature signal to obtain a fused feature signal, and converting the fused feature signal to obtain a quasi-heart rate and a quasi-vibration frequency.

2. The method according to claim 1, wherein performing the extraction processing on the window video to obtain an eye feature signal, a mouth feature signal, an eyebrow feature signal, and a chin feature signal, comprising:
    using the model to predict the window video to generate face key points, the face key points including contour key points and specific part key points;
    extracting eye key points, mouth key points, the ROI between the eyebrows, and ROI of the chin respectively from the face key points;
    performing dimension reduction processing on the eye key point and the mouth key point respectively to obtain an eye feature signal and a mouth feature signal;
    performing feature extraction on the ROI between the eyebrows and the ROI of the chin, respectively to obtain an eyebrow color signal and a chin color signal; and
    performing noise reduction processing on the eyebrow color signal and the chin color signal respectively to obtain an eyebrow feature signal and a chin feature signal.

3. The method according to claim 1, wherein performing the conversion processing on the fusion feature signal to obtain the quasi-heart rate and the quasi-vibration frequency, comprising:
  performing noise reduction processing on the fusion feature signal to obtain a smooth feature signal;
  performing blind source separation on the smooth feature signal, and converting signal components of the smooth feature signal after the blind source separation into frequencies for obtaining a plurality of frequencies;
  selecting, based on a body heart rate range, a pre-heart rate from the plurality of frequencies, and averaging the selected pre-heart rate to obtain a quasi-heart rate; and
  selecting, based on the eye vibration frequency range and mouth vibration frequency range, a pre-vibration frequency from the plurality of frequencies, and averaging the selected pre-vibration frequencies to obtain a quasi-vibration frequency.

4. The method according to claim 1, wherein the selecting the target heart rate from the plurality of quasi-heart rates and selecting the target vibration frequency from the plurality of quasi-vibration frequencies comprises:
  determining a median of the plurality of quasi-heart rates and a mean value of the plurality of quasi-vibration frequencies;
  determining, for each of the plurality of quasi-heart rate, a difference between the each quasi-heart rate and a corresponding median, and determining whether the difference is greater than a first preset heart rate threshold, and in response to the difference being greater than the first preset heart rate threshold, removing the corresponding quasi-heart rate from the plurality of quasi-heart rates to obtain the target heart rate; and
  determining, for each of the quasi-vibration frequencies, a difference between the quasi-vibration frequency and a corresponding median, and determining whether the difference is greater than a first preset vibration threshold, and in response to the difference being greater than the first preset vibration threshold, removing the corresponding quasi-vibration frequency from the plurality of quasi-vibration frequencies to obtain the target vibration frequency.

5. The method according to claim 1, wherein the detecting the target heart rate and the target vibration frequency, and determining that the target object is in a fatigue state according to the detection result comprises:
  obtaining a normal heart rate and a normal vibration frequency of the target object when the target object is in a non-fatigue state;
  determining a difference between the normal heart rate and the target heart rate and a difference between the normal vibration frequency and the target vibration frequency respectively;
  determining, within preset measurement times, in response the difference corresponding to the target heart rate measured each time being greater than a second preset heart rate threshold and the difference corresponding to the target vibration frequency measured each time being greater than a second preset vibration threshold, that the target object is in a mild fatigue state.

6. The method according to claim 1, wherein the detecting the target heart rate and the target vibration frequency, and determining that the target object is in a fatigue state according to the detection result comprises:
  obtaining a normal heart rate and a normal vibration frequency of the target object when the target object in a non-fatigue state;
  determining a difference between the normal heart rate and the target heart rate and a difference between the normal vibration frequency and the target vibration frequency respectively;
  determining, within preset measurement times, in response to the difference corresponding to the target heart rate measured each time being greater than a third preset heart rate threshold and a difference corresponding to each measured target vibration frequency being greater than a third preset vibration threshold, that the target object is in a microsleep state.

7. A fatigue measurement apparatus, comprising:
  an acquisition module configured to obtain a face video of a target object;
  a processing module configured to process the face video to obtain a plurality of quasi-heart rates and a plurality of quasi-vibration frequencies, wherein the quasi-heart rate is obtained through one or more of a region of interest (ROI) between eyebrows and an ROI of chin, and wherein the quasi-vibration frequencies is obtained through one or more of an ROI of eyes and an ROI of mouth;
  a selection module configured to select a target heart rate from the plurality of quasi-heart rates and a target vibration frequency from the plurality of quasi-vibration frequencies; and
  a detection module configured to detect the target heart rate and the target vibration frequency, and determine that the target object is in a fatigue state according to the detection result,
  wherein the processing module comprises:
    a dividing unit configured to divide the face video into a plurality of window videos according to a time window of a specific step size; and
    a processing unit configured to, for each of the window videos, perform extraction processing on the each window videos to obtain an eye feature signal, a mouth feature signal, an eyebrow feature signal, and a chin feature signal, fuse the eye feature signal, the mouth feature signal, the eyebrow feature signal, and the chin feature signal to obtain a fusion feature signal, and converting the fusion feature signal to obtain a quasi-heart rate and a quasi-vibration frequency.

8. The apparatus according to claim 7, wherein the processing unit comprises:
  a prediction subunit configured to use the model to predict the window video, and generate face key points, where the face key points include contour key points and specific part key points; a first extraction unit configured to extract eye key points, mouth key points, an ROI between the eyebrows, and an ROI of the chin from the face key points respectively;
  a dimension reduction subunit configured to perform dimension reduction processing on the eye key points and the mouth key points respectively to obtain an eye feature signal and a mouth feature signal;
  a second extraction subunit configured to perform feature extraction processing on the ROI between the eyebrows and the ROI of the chin, respectively, to obtain an eyebrow color signal and a chin color signal; and
  a third noise reduction sub-unit configured to perform noise reduction processing on the eyebrow color signal and the chin color signal respectively, to obtain the
eyebrow feature signal and the chin feature signal.

9. The apparatus according to claim 7, wherein the processing unit further comprises:
a second noise reduction subunit configured to perform noise reduction processing on the fused feature signal to obtain a smooth feature signal;
a blind source separation subunit configured to blindly perform noise reduction on the smooth feature signal source separation, and convert signal components after blind source separation into frequencies to obtain a plurality of frequencies;
a selection subunit configured to select a pre-heart rate from the plurality of frequencies based on the body's heart rate range, and average the selected pre-heart rate to obtain a quasi-heart rate, select pre-vibration frequencies from the plurality of frequencies based on an eye vibration frequency range and a mouth vibration frequency range, and average the selected pre-vibration frequencies to obtain a quasi-vibration frequency.

10. The apparatus according to claim 7, wherein the selection module comprises:
a determination unit configured to determine a mean value of the plurality of quasi-heart rates and a mean value of the plurality of quasi-vibration frequencies;
a first selection subunit configured to, for any quasi-heart rate, determine a difference between the quasi-heart rate and the corresponding mean value, determine whether the difference is greater than a first preset heart rate threshold, and in response to the difference being greater than the first preset heart rate threshold, remove the quasi-heart rate from the plurality of quasi-heart rates to obtain a target heart rate;
a second selection subunit configured to, for any quasi-vibration frequency, determine a difference between the quasi-vibration frequency and the corresponding median, determine whether the difference is greater than a first preset vibration threshold, and in response to the difference being greater than the first preset vibration threshold, remove the quasi-vibration frequency from the plurality of quasi-vibration frequencies to obtain a target vibration frequency.

11. The apparatus according to claim 7, wherein the detection module comprises:
an acquisition unit configured to acquire a normal heart rate and a normal vibration frequency of the target object when the target object is in a non-fatigue state;
a difference unit configured to determine a difference between the normal heart rate and the target heart rate and a difference between the normal vibration frequency and the target vibration frequency, respectively; and
a determining unit configured to determine that the target object is in a state of mild fatigue, in response to the difference corresponding to the target heart rate measured each time within preset measurement times being greater than a second preset heart rate threshold and the difference corresponding to the target vibration frequency measured each time within preset measurement times being greater than a second preset vibration threshold.

12. A non-transitory computer-readable medium for storing a computer program, when executed by a processor, causing the processor to:
obtain a face video of a target object;
process the facial video to obtain a plurality of quasi-heart rates and a plurality of quasi-vibration frequencies,
wherein the quasi-heart is obtained through one or more of a region of interest (ROI) between eyebrows and an ROI of chin, and the quasi-vibration frequency is obtained through one or more of an ROI of eyes and an ROI of mouth;
select a target heart rate from the plurality of quasi-heart rates and a target vibration frequency from the plurality of quasi-vibration frequencies; and
detect the target heart rate and the target vibration frequency, and determine, according to the detection result, that the target object is in a fatigue state,
wherein when processing the face video to obtain the plurality of quasi-heart rates and the plurality of quasi-vibration frequencies, the processor is further caused to:
divide the face video into a plurality of window videos according to a time window of a specific step size; and
perform, for each window video of the plurality of window videos, extraction processing on the each window video to obtain an eye feature signal, a mouth feature signal, an eyebrow feature signal, and a chin feature signal, fusing the eye feature signal, the mouth feature signal, the eyebrow feature signal, and the chin feature signal to obtain a fused feature signal, and convert the fused feature signal to obtain a quasi-heart rate and a quasi-vibration frequency.

13. The non-transitory computer-readable medium according to claim 12, wherein when performing the extraction processing on the window video to obtain an eye feature signal, a mouth feature signal, an eyebrow feature signal, and a chin feature signal, the processor is further caused to:
use the model to predict the window video to generate face key points, the face key points including contour key points and specific part key points;
extract eye key points, mouth key points, the ROI between the eyebrows, and ROI of the chin respectively from the face key points;
perform dimension reduction processing on the eye key point and the mouth key point respectively to obtain an eye feature signal and a mouth feature signal;
perform feature extraction on the ROI between the eyebrows and the ROI of the chin, respectively to obtain an eyebrow color signal and a chin color signal; and
perform noise reduction processing on the eyebrow color signal and the chin color signal respectively to obtain an eyebrow feature signal and a chin feature signal.

14. The non-transitory computer-readable medium according to claim 12, wherein when performing the conversion processing on the fusion feature signal to obtain the quasi-heart rate and the quasi-vibration frequency, the processor is further caused to:
perform noise reduction processing on the fusion feature signal to obtain a smooth feature signal;
perform blind source separation on the smooth feature signal, and converting signal components of the smooth feature signal after the blind source separation into frequencies for obtaining a plurality of frequencies;
select, based on a body heart rate range, a pre-heart rate from the plurality of frequencies, and average the selected pre-heart rate to obtain a quasi-heart rate; and
select, based on the eye vibration frequency range and mouth vibration frequency range, a pre-vibration frequency from the plurality of frequencies, and average the selected pre-vibration frequencies to obtain a quasi-vibration frequency.

15. The non-transitory computer-readable medium according to claim 12, wherein when selecting the target heart rate from the plurality of quasi-heart rates and selecting the target vibration frequency from the plurality of quasi-vibration frequencies, the processor is further caused to:
- determine a median of the plurality of quasi-heart rates and a mean value of the plurality of quasi-vibration frequencies;
- determine, for each of the plurality of quasi-heart rate, a difference between the each quasi-heart rate and a corresponding median, and determining whether the difference is greater than a first preset heart rate threshold, and in response to the difference being greater than the first preset heart rate threshold, remove the corresponding quasi-heart rate from the plurality of quasi-heart rates to obtain the target heart rate; and
- determine, for each of the quasi-vibration frequencies, a difference between the quasi-vibration frequency and a corresponding median, and determining whether the difference is greater than a first preset vibration threshold, and in response to the difference being greater than the first preset vibration threshold, remove the corresponding quasi-vibration frequency from the plurality of quasi-vibration frequencies to obtain the target vibration frequency.

16. The non-transitory computer-readable medium according to claim 12, wherein when detecting the target heart rate and the target vibration frequency, and determining that the target object is in a fatigue state according to the detection result, the processor is further caused to:
- obtain a normal heart rate and a normal vibration frequency of the target object when the target object is in a non-fatigue state;
- determine a difference between the normal heart rate and the target heart rate and a difference between the normal vibration frequency and the target vibration frequency respectively;
- determine, within preset measurement times, in response the difference corresponding to the target heart rate measured each time being greater than a second preset heart rate threshold and the difference corresponding to the target vibration frequency measured each time being greater than a second preset vibration threshold, that the target object is in a mild fatigue state.

17. The non-transitory computer-readable medium according to claim 12, wherein when detecting the target heart rate and the target vibration frequency, and determining that the target object is in a fatigue state according to the detection result, the processor is further caused to:
- obtain a normal heart rate and a normal vibration frequency of the target object when the target object in a non-fatigue state;
- determine a difference between the normal heart rate and the target heart rate and a difference between the normal vibration frequency and the target vibration frequency respectively;
- determine, within preset measurement times, in response to the difference corresponding to the target heart rate measured each time being greater than a third preset heart rate threshold and a difference corresponding to each measured target vibration frequency being greater than a third preset vibration threshold, that the target object is in a microsleep state.

* * * * *